United States Patent [19]

Teisseire et al.

[11] 4,163,109
[45] Jul. 31, 1979

[54] PROCESS FOR THE PREPARATION OF CYCLIC KETONES

[75] Inventors: Paul J. Teisseire, Grasse; Marcel Plattier, Antibes; Edouard Giraudi, La Roquette sur Siagne, all of France

[73] Assignee: Societe Anonyme Roure Bertrand Dupont, Paris, France

[21] Appl. No.: 815,213

[22] Filed: Jul. 13, 1977

[30] Foreign Application Priority Data

Jul. 16, 1976 [CH] Switzerland ............... 9136/76
Nov. 8, 1976 [CH] Switzerland ............... 14030/76

[51] Int. Cl.$^2$ ............... C07C 69/74; C07C 67/32
[52] U.S. Cl. ............... 560/122; 560/126
[58] Field of Search ............... 560/126, 122

[56] References Cited

U.S. PATENT DOCUMENTS

| | | | |
|---|---|---|---|
| 3,158,644 | 11/1964 | Demole et al. | 260/468 K |
| 3,754,016 | 8/1973 | Oberhansli | 260/468 K |
| 3,823,190 | 7/1974 | Oberhansli | 260/586 R |
| 3,941,828 | 3/1976 | Buchi | 560/468 K |
| 3,970,682 | 7/1976 | Plattier et al. | 560/122 |
| 3,981,891 | 9/1976 | Celli et al. | 560/122 |
| 4,014,919 | 3/1977 | Johnson et al. | 260/468 K |

FOREIGN PATENT DOCUMENTS 1351919 5/1974 United Kingdom .

*Primary Examiner*—Jane S. Myers
*Attorney, Agent, or Firm*—Wallenstein, Spangenberg, Hattis & Strampel

[57] ABSTRACT

A process for the preparation of compounds of the formula I

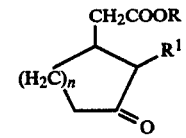

by reacting of a compound of the formula II

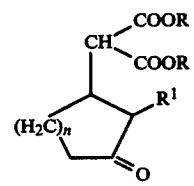

with up to 1.5 molar equivalent of water at elevated temperature. R represents an alkyl group containing 1 to 3 carbon atoms, $R^1$ represents an alkyl or alkenyl group containing 3 to 6 carbon atoms and n represents 1 or 2.

9 Claims, No Drawings

PROCESS FOR THE PREPARATION OF CYCLIC KETONES

DETAILED DESCRIPTION OF THE INVENTION

The present invention is concerned with a process for the preparation of compounds of the general formula

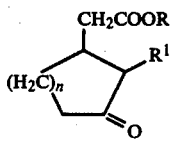  I in which R represents an alkyl group containing 1 to 3 carbon atoms, preferably methyl or ethyl, $R^1$ represents an alkyl or alkenyl group containing 3 to 6 carbon atoms and n represents 1 or 2,
wherein a compound of the general formula

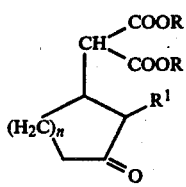  II in which R, $R^1$ and n have the given above,
is reacted with up to 1.5 molar equivalents of water, per molar equivalent of compound of formula II, at an elevated temperature.

The reaction is advantageously carried out at an elevated temperature, which should however lie sufficiently below the decomposition temperature of the starting material or of the end product to minimise decomposition; on the other hand the temperature should nevertheless be high enough to ensure attainment of a high yield. The reaction is preferably carried out at a temperature of 200° to 260°. It has been found that the yields decrease with reducing temperature, so that at a temperature of 160° the yield may fall to about 60%. The reaction is preferably carried out at substantially the ambient pressure.

In order to obtain a high yield, it is preferable to carry out the reaction using at least one molar equivalent of water per molar equivalent of starting substance of general formula II used. If less than one molar equivalent of water is used, the yield will necessarily be lower. Any increase in the quantity of water used will likewise cause a reduction in the yield, because of undesirable secondary reactions. In general, from 1 to 1.5 molar equivalents of water, preferably from 1.1 to 1.3, are advantageously used without there being any serious negative effect on the yield. The use of more than 2.0 mols of water per mol of malonate will however cause a serious reduction in the yield.

The reaction can normally be completed within three hours the reaction time preferably being from 1 to 2.5 hours.

The two symbols R can represent the groups methyl, ethyl, n-propyl, isopropyl, etc. The two groups R will normally be identical, since the starting substances having different groups R are more complicated to prepare.

The group $R^1$ can be any linear or branched alkyl or alkenyl group containing 3 to 6 carbon atoms such as, for example, n-propyl, isopropyl, n-butyl, t-butyl, n-pentyl, n-hexyl, n-2-butenyl, n-2-cis-pentenyl, n-2-trans-pentenyl, n-3-cis-hexenyl, etc.

The process of the invention is preferably carried out by heating a compound of general formula I to the desired reaction temperature, then adding the water drop by drop until the reaction is complete.

The process can be carried out equally well with the compounds of general formula I in which n=1 as with those where n=2, that is to say, the relevant cyclopentanones or cyclohexanones.

The process of the present invention is particularly appropriate for the preparation of dihydromethyl-jasmonate which is a particularly valuable odoriferous substance which imparts a jasmin note to odoriferous compositions. The compounds of general formula I exist in various stereoisomeric forms, and the process of the invention can be used for the preparation of any particular isomer.

The invention is illustrated by the following Examples.

EXAMPLE 1

142 g of 2-pentanyl-3-oxo-cyclopentyl methyl malonate are charged into a 4-necked 250 ml flask provided with a stirrer a dropping funnel, a thermometer and a Vigreux column, this latter being equipped with a reflux condenser. The mixture is heated until the mass reaches a temperature of 200° and 12 g of water are then added dropwise over 2 hours. During the addition, 19 ml of methanol is distilled off and carbon dioxide is removed. The reaction mass is cooled, 70 ml of toluene added, the solution transferred into a separating funnel and washed twice with 50 ml of an aqueous 9% solution of sodium bicarbonate, then with water until neutral. The toluene is distilled off on a water-bath under a pressure of 100 mm of mercury. The crude keto ester is re-distilled in vacuo; there being thus obtained 93.8 g (yield=83%) of 2-pentanyl-3-oxo-cyclopentyl methyl acetate distilling between 122° and 126° under 1 mm of Hg. The product has the following characteristics: $n_D^{18}=1.4570$ and d 20/20=1000.

EXAMPLE 2

The apparatus of Example 1 is charged with 80.15 g of 2-pentanyl-3-oxocyclopentyl methyl malonate. The mass is heated to 200°. 5.7 g of water are then added dropwise over two hours. During the addition 5.5 ml of methanol is distilled off and the carbon dioxide is removed. After working up as described in example 1, there are obtained 48.1 g (yield=74%) of 2-pentanyl-3-oxocyclopentanyl methyl acetate distilling between 110° and 113° under a pressure of 0.7 mm of Hg.

EXAMPLE 3

The apparatus of Example 1 is charged with 70 g of 2-pentanyl-3-oxocyclopentyl methyl malonate (0.246 mol). The mass is treated to 260°. 5.32 g of water are then added dropwise over two hours. During the addition 7.1 g of methanol is distilled off and carbon dioxide is removed. After working up as described in Example 1, 36.6 g of 2-pentanyl-3-oxocyclopentanyl methyl acetate are obtained distilling between 108° and 109° under a pressure of 0.4 mm of Hg.

EXAMPLE 4

The apparatus of Example 1 is charged with 201.1 g of 2-hexyl-3-oxocyclopentyl methyl malonate. The mass is heated to 200°. 16.4 g of water are then added dropwise over two hours. During the addition, 21.4 g of methanol distills off and carbon dioxide is removed. After working up as described in Example 1 125.1 g (yield=77%) of 2-hexyl-3-oxocyclopentyl methyl acetate are obtained distilling between 124° and 126° under a pressure of 0.4 mm of Hg. The product has the following characteristics: $n_D^{21}=1.4563$ and d 20/20=0.988.

EXAMPLE 5

The apparatus of Example 1 is charged with 203.8 g of 2-propyl-3-oxocyclopentyl methyl malonate. The mass is heated to 200°. 18.6 g of water are then added dropwise over two hours. During the addition 29.3 g of methanol distills off and carbon dioxide is removed. After working up as described in Example 1 116.2 g of 2-propyl-3-oxocyclopentyl methyl acetate (yield=73.7%) is obtained distilling between 95° and 100° under a pressure of 0.5 mm of Hg. The product has the following characteristics: $n_D^{21}=1.4547$ and d 20/20=1.025.

EXAMPLE 6

The apparatus of Example 1 is charged with 119 g of 2-amyl-3-oxocyclopentyl ethyl malonate. The mass is heated to 200°. 8.92 g of water are then added dropwise over 3 hours. During the addition, 21.5 g of ethanol distills off and carbon dioxide is removed. After working up as described in Example 1 67.8 g of 2-amyl-3-oxocyclopentyl ethyl acetate (yield=73.7%) are obtained distilling between 117° and 124° under a pressure of 0.6 mm of Hg. The product has the following characteristics: $n_D^{22.5}=1.4523$ and d 20/20=0.9830.

EXAMPLE 7

The apparatus of Example 1 is charged with 87.4 g of 2-(cis-penten-2-yl)-3-oxo-cyclopentyl methyl malonate. The mass is heated to 200°. 7.25 g of water are then added dropwise over 1½ hours. During the addition 9.1 g of methanol distills off and carbon dioxide is removed. After working up as described in Example 1, 57.6 g of 2-(cis-penten-2-yl)-3-oxocyclopentyl methyl acetate is obtained (yield=83%) distilling at 90° under a pressure of 0.05 mm of Hg. The product has the following characteristics: $n_D^{22}=1.4728$ and d 20/20=1.0232

EXAMPLE 8

The apparatus of Example 1 is charged with 34.5 g of 2-amyl-3-oxocyclohexyl methyl malonate (0.116 mol). The mass is heated to 200°. 2.7 g of water are then added dropwise over 40 minutes. During the addition, 4.1 g of methanol distills off and carbon dioxide is removed. After working up as described in Example 1, 20.3 g of 2-amyl-3-oxo-cyclohexyl methyl acetate is obtained (yield=73%) distilling between 98° and 103° under a pressure of 0.1 mm of Hg. The product has the following characteristics: $n_D^{19}=1.4672$ and d 20/20=1.0017.

What is claimed is:

1. A process for the preparation of compounds of the formula

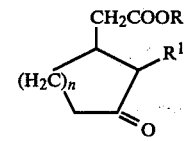

in which R represents an alkyl group containing 1 to 3 carbon atoms, $R^1$ represents an alkyl or alkenyl group containing 3 to 6 carbon atoms and n represents 1 or 2, wherein a compound of the general formula

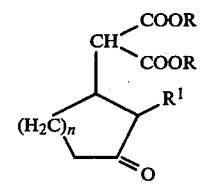

in which R, $R^1$ and n have the meanings given above is reacted with from 1 to 1.5 molar equivalents of water, per molar equivalent of compound of formula II, at such an elevated temperature as to produce a yield of not less than about 60% of the compound of formula I.

2. A process according to claim 1, wherein the reaction is carried out at a temperature of from 200° to 260°.

3. A process according to claim 1, wherein from about 1 to about 1.3 molar equivalents of water are used per molar equivalent of compound of formula II used.

4. A process according to claim 1, which is carried out at substantially ambient pressure.

5. A process according to claim 1, wherein $R^1$ represents a cis-2-n-pentenyl group.

6. A process according to claim 1, wherein $R^1$ represents a n-pentyl group.

7. A process according to claim 1, wherein R represents a methyl group.

8. A process according to claim 1, wherein R represents an ethyl group.

9. A process according to claim 1, wherein R represents a methyl group, $R^1$ represents a pentyl group and n is 1.

* * * * *